United States Patent

Fujimoto

[11] Patent Number: 6,139,858
[45] Date of Patent: Oct. 31, 2000

[54] TERMITE-CONTROLLING AGENT

[75] Inventor: Izumi Fujimoto, Minoo, Japan

[73] Assignee: Sumitomo Chemical Company Limited, Osaka, Japan

[21] Appl. No.: 09/472,956

[22] Filed: Dec. 27, 1999

[51] Int. Cl.[7] .................................... A01N 25/10
[52] U.S. Cl. ............... 424/405; 424/409; 424/411; 424/412; 424/413; 424/4 A; 424/DIG. 11; 514/376
[58] Field of Search ...................... 424/405, 409, 424/411–416, 418, DIG. 11; 514/374, 376, 360

[56] References Cited

U.S. PATENT DOCUMENTS

| | | | |
|---|---|---|---|
| 891,440 | 6/1908 | Rader | 428/537.7 |
| 5,466,703 | 11/1995 | Kudoh et al. | |
| 5,573,760 | 11/1996 | Thorne et al. | 424/84 |

FOREIGN PATENT DOCUMENTS 93-22297   11/1993   WIPO .

*Primary Examiner*—Neil S. Levy
*Attorney, Agent, or Firm*—Sughrue, Mion, Zinn, Macpeak & Seas, PLLC

[57] ABSTRACT

A termite-controlling agent comprising 5-tert-butyl-2-[2-(2,6-difluorophenyl)-4,5-dihydrooxazol-4-yl]phenetole as an active ingredient and cellulose, which can be a sheet formulation or a powdery formulation, has an excellent efficiency for controlling termites.

5 Claims, No Drawings

TERMITE-CONTROLLING AGENT

FIELD OF THE INVENTION

The present invention relates to a termite-controlling agent.

BACKGROUND OF THE INVENTION

WO93/22297 shows 5-tert-butyl-2-[2-(2,6-difluorophenyl)-4,5-dihydrooxazol-4-yl]phenetole (hereinafter referred to as "etoxazole") of the formula:

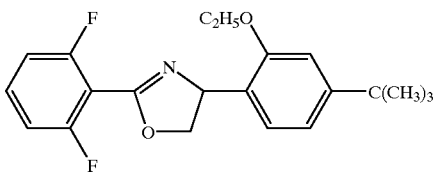

as an active ingredient of insecticides. Etoxazole is developed as an active ingredient of miticide and insecticide for agricultural use.

The object of the present invention is to provide a new use of etoxazole, namely a use as an active ingredient for a termite-controlling agent having an excellent efficiency.

SUMMARY OF THE INVENTION

The present invention provides a termite-controlling agent which comprises etoxazole as an active ingredient and cellulose.

The termite-controlling agent can be a sheet formulation or a powdery formulation.

DETAILED DESCRIPTION OF THE INVENTION

When the present termite-controlling agent is a powdery formulation, it generally contains 0.005 to 20% by weight of etoxazole and 30 to 99.995% by weight of cellulose powder. Cellulose powder can be obtained by pulverizing after acidic hydrolysis of lumber cellulose. Further, naturally obtained cellulose materials such as wood powder may be utilized as cellulose powder.

The present termite-controlling agent that is a powdery formulation can contain powder carriers. Examples of the powder carrier utilized in the present invention include inorganic powders such as synthetic hydrated silica, anhydrous silica, aluminum oxide, kaolin, talc, titanium oxide and magnesium carbonate; synthetic resin powders such as polyurethane, polyamide and polypropylene; and salts such as calcium stearate. The amount of the powder carrier is generally 0 to 69.995% by weight in the present termite-controlling agent.

The powdery formulation can be usually produced by mixing and pulverizing etoxazole and cellulose powder, and optionally powder carriers.

The present termite-controlling agent can be an aerosol formulation containing above-mentioned powdery formulation. The aerosol formulation usually comprises the powdery formulation and propellant, and optionally solvent, wherein the amount of the powdery formulation and the propellant in the aerosol formulation is usually 0.1 to 10% and 20 to 90% by weight respectively. Said solvents are exemplified by esters such as isopropyl myristate, isopropyl palmitate, isopropyl decanoate, isopropyl laurate and so on; and alcohols such as ethanol, isopropyl alcohol and so on.

When the present termite-controlling agent is a sheet formulation, it generally contains 0.01 to 20% by weight of etoxazole in the sheet formulation.

The sheet formulation can be produced by having etoxazole supported on a cellulose paper by usual methods. For example, a solution or dispersion containing etoxazole is spread on a cellulose paper and dried. The solution or dispersion can be prepared by dissolving etoxazole in a suitable organic solvent and optionally diluting it with water containing a surfactant or dispersant.

Examples of the termites effectively controlled by the present invention include Mastotermitidae; Termopsidae such as Zootermopsis spp., Archotermopsis spp., Hodotermopsis spp., Porotermes spp. and Stolotermes spp.; Kalotermitidae such as Kalotermes spp., Neotermes spp., Cryptotermes spp., Incisitermes spp. and Glyptotermes spp.; Hodotermitidae such as Hodotermes spp., Microhodotermes spp. and Anacanthotermes spp.; Rhinotermitidae such as Reticulitermes spp., Heterotermes spp., Coptotermes spp. and Schedolinotermes spp.; Serritermitidae; and Termitidae such as Amitermes spp., Drepanotermes spp., Hopitalitermes spp., Trinervitermes spp., Macrotermes spp., Odontotermes spp., Microtermes spp., Nasutitermes spp., Pericapritermes spp. and Anoplotermes spp.

Typical examples of the termites species objected in the present invention include *Recticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticultermes flaviceps amamianus*, Reticulitermes sp. (Kanmonshiroari), *Nasutitermes takasagoensis, Pericapritermes nitobei* and *Sinocapritermes mushae*.

The present termite-controlling agent is applied to termite tunnel, lumber damaged by termites or a locus termites inhabit, such as soil, wood, and so on. For the application to termite tunnel, a part of the termite tunnel is destroyed and the present termite-controlling agent is applied inside the termite tunnel. Further, for the application to lumber damaged by termites or locus where termites inhabit, the present termite-controlling agent is applied by pasting the damaged lumber with a sheet formulation or distributing a powdery formulation to the lumber or the locus if necessary holed.

The application dosage of etoxazole depends on a degree of damage and the other conditions. In case that the present termite-controlling agents are applied on the soil or wood, the dosage of etoxazole is usually 0.1 g to 100 g, preferably 1 g to 30 g per 1 $m^2$. Further, in case that the present termite-controlling agents are applied to a termite tunnel or the place damaged by termites, the dosage of etoxazole is usually 0.01 to 1000 g, preferably 0.1 to 100 g.

EXAMPLES

Next, the present invention is explained by formulation examples and test examples in detail.

Formulation Example 1

One part by weight of etoxazole and 99 parts by weight of crystallized cellulose powder (Avicel produced by Asahi Chemical Industry Co., Ltd.) are mixed to give a present termite-controlling agent.

Formulation Example 2

Five parts by weight of etoxazole and 95 parts by weight of crystallized cellulose powder (Avicel produced by Asahi Chemical Industry Co., Ltd.) are mixed to give a present termite-controlling agent.

Formulation Example 3

Five parts by weight of etoxazole and 95 parts by weight of wood powder are mixed to give a present termite-controlling agent.

Formulation Example 4

One-half (0.5) part by weight of etoxazole, 40 parts by weight of crystallized cellulose and 59.5 parts by weight of talc are mixed to give a present termite-controlling agent.

Formulation Example 5

Two parts by weight of etoxazole, 50 parts by weight of crystallized cellulose and 48 parts by weight of clay are mixed to give a present termite-controlling agent.

Formulation Example 6

Two mililiter (2 mL) of acetone solution containing 15 mg of etoxazole is soaked on a filter paper (cellulose paper, 9 cm in diameter) and dried to give a present termite-controlling agent.

Formulation Example 7

Five mililiter (5 mL) of acetone solution containing 50 mg of etoxazole is soaked on a kraft paper (cellulose paper, 15 cm×15 cm) and dried to give a present termite-controlling agent.

Next, test examples are shown below.

Test Example 1

Filter paper (cellulose paper produced by Advantec Corp,, 33 mm in diameter) was soaked with 1 mL of acetone solution containing 2 mg of etoxazole and dried. Said filter paper was put in a white plastic cup of 35 mm in diameter having 5 holes, where termites can pass through, on the sides and bottom. The white plastic cup was put inside a large cup and 100 Formosan subterranean termites (*Coptotermes formosanus*) were released inside the large cup. While moisture was supplied into the large cup, the mortality was observed. As a result, the mortality after 9 weeks was 93%.

Test Example 2

Ten miligrams (10 mg) of the present termite-controlling agent obtained according to Formulation Example 2 were spread on a aluminum dish of 9 cm in diameter. Said aluminum dish was put in a plastic cup of 5 cm in diameter having wet filter paper on the bottom. Twenty Formosan subterranean termites (*Coptotermes formosanus*) were released inside the aluminum dish and the mortality was observed after 3 hours and 18 hours. As a result, the percent moribund after 3 hours was 0%, but all the termites were dead or moribund after 18 hours.

Further, 19 dead termites were gathered and transferred to a plastic petri dish of 9 cm in diameter where clean wet filter paper was spread on the bottom. The same number of healthy Formosan subterranean termites were released inside the plastic petri dish. After 19 days, all the termites were observed to be dead.

Test Example 3

Ten miligrams (10 mg) of the present termite-controlling agent obtained according to Formulation Example 3 were spread on a aluminum dish of 9 cm in diameter. Said aluminum dish was put in a plastic cup of 5 cm in diameter having wet filter paper on the bottom. Fifteen Formosan subterranean termites (*Coptotermes formosanus*) were released inside the aluminum dish and the mortality was observed after 3 hours and 18 hours. As a result, the percent moribund after 3 hours was 6.7%, but fourteen termites (93%) were dead or moribund after 18 hours.

Further, 14 dead termites were gathered and transferred to a plastic petri dish of 9 cm in diameter where clean wet filter paper was spread on the bottom. The same number of healthy Formosan subterranean termites were released inside the plastic petri dish. After 21 days, all the termites were observed to be dead.

As shown in the test examples 2 and 3 above, the present termite-controlling agent gave low mortality or percent moribund after 3 hours but excellent efficiency after 18 hours. Further, a transmission of toxicity was observed.

The present termite-controlling agent shows late efficacy. Therefore, termites in contact with the present termite-controlling agent tends to return their nest and die there, and as a result many termites in the nest contact with the dead bodies and they can also be exterminated.

What is claimed is:

1. A method for controlling termites which comprises applying an effective amount of the termite-controlling agent which comprises 5-tert-butyl-2-[2-(2,6-difluorophenyl)-4,5-dihydrooxazol-4-yl]phenetole as an active ingredient and cellulose to termite tunnel, lumber damaged by termites or a locus termites inhabit.

2. A method according to claim 1, wherein the termite-controlling agent is formed to a powdery formulation.

3. A method according to claim 2, wherein the termite-controlling agent comprises 0.005 to 20% by weight of 5-tert-butyl-2-[2-(2,6-difluorophenyl)-4,5-dihydrooxazol-4-yl)phenetole and 30 to 99.995% by weight of cellulose.

4. A method according to claim 1, wherein the termite-controlling agent is formed to a sheet formulation.

5. A method according to claim 1, wherein 0.01 to 100 g of 5-tert-butyl-2-[2-(2,6-difluorophenyl)-4,5-dihydrooxazol]phenetole per 1 $m^2$ of cellulose paper is applied.

\* \* \* \* \*